United States Patent
Ohno et al.

(10) Patent No.: US 8,303,517 B2
(45) Date of Patent: Nov. 6, 2012

(54) MEDICAL APPARATUS AND LIVING TISSUE FREEZING AND HARVESTING APPARATUS

(75) Inventors: Shinichi Ohno, Chuo (JP); Koji Shimomura, Hachioji (JP)

(73) Assignees: University of Yamanashi, Yamanashi (JP); Olympus Medical Systems Corp., Tokyo (JP)

( * ) Notice: Subject to any disclaimer, the term of this patent is extended or adjusted under 35 U.S.C. 154(b) by 227 days.

(21) Appl. No.: 12/720,014

(22) Filed: Mar. 9, 2010

(65) Prior Publication Data
US 2010/0160813 A1 Jun. 24, 2010

Related U.S. Application Data

(63) Continuation of application No. PCT/JP2008/058790, filed on May 13, 2008.

(30) Foreign Application Priority Data

Sep. 10, 2007 (JP) ................................ 2007-234671

(51) Int. Cl.
*A61B 10/00* (2006.01)
*A61B 18/18* (2006.01)

(52) U.S. Cl. ............ 600/564; 600/567; 606/20; 606/21; 606/22; 606/23

(58) Field of Classification Search .......... 600/562–569, 600/153, 154, 156; 606/20–26
See application file for complete search history.

(56) References Cited

U.S. PATENT DOCUMENTS

| | | | | |
|---|---|---|---|---|
| 4,784,133 A | * | 11/1988 | Mackin | 606/7 |
| 5,133,360 A | * | 7/1992 | Spears | 600/567 |
| 6,540,694 B1 | | 4/2003 | Van Bladel et al. | |
| 2002/0045842 A1 | | 4/2002 | Van Bladel et al. | |
| 2003/0195436 A1 | | 10/2003 | Van Bladel et al. | |
| 2004/0267248 A1 | * | 12/2004 | Duong et al. | 606/21 |
| 2007/0055173 A1 | * | 3/2007 | DeLonzor et al. | 600/564 |
| 2007/0167938 A1 | * | 7/2007 | Zvuloni et al. | 606/21 |
| 2007/0191732 A1 | | 8/2007 | Voegele | |
| 2007/0213632 A1 | * | 9/2007 | Okazaki et al. | 600/562 |

FOREIGN PATENT DOCUMENTS

| | | |
|---|---|---|
| EP | 1 818 018 A1 | 8/2007 |
| JP | 09-238893 | 9/1997 |
| JP | 2004-511292 | 4/2004 |
| JP | 2005-278715 | 10/2005 |
| JP | 2006-006389 | 1/2006 |
| JP | 2007-222618 | 9/2007 |
| WO | WO 02/32318 A1 | 4/2002 |

OTHER PUBLICATIONS

International Search Report dated Jun. 17, 2008.

* cited by examiner

*Primary Examiner* — Max Hindenburg
*Assistant Examiner* — Adam Eiseman
(74) *Attorney, Agent, or Firm* — Scully, Scott, Murphy & Presser, P.C.

(57) ABSTRACT

A first trocar as an medical apparatus includes an insertion hole having a projection opening for leading out a biopsy forceps into a body of a subject, a lid body for blocking the projection opening of the insertion hole, and a cooling sheet for cryogenically cooling a biopsy portion arranged in the vicinity of the lid body in a state where the biopsy forceps is stored in the insertion hole, and is capable of easily harvesting a living tissue while retaining morphological change of tissues in a living body under various hemodynamics.

6 Claims, 8 Drawing Sheets

MEDICAL APPARATUS AND LIVING TISSUE FREEZING AND HARVESTING APPARATUS

CROSS REFERENCE TO RELATED APPLICATION

This application is a continuation application of PCT/JP2008/058790 filed on May 13, 2008 and claims benefit of Japanese Application No. 2007-234671 filed in Japan on Sep. 10, 2007, the entire contents of which are incorporated herein by this reference.

BACKGROUND OF THE INVENTION

1. Field of the Invention

The present invention relates to a medical apparatus and a living tissue freezing and harvesting apparatus that instantly freeze and harvest a living tissue.

2. Description of the Related Art

In recent years, there has been an increasing demand for a definite diagnosis made on a harvested body tissue of a patient at a pathological department. When making a definite diagnosis, an image of a region considered to be abnormal is observed by an endoscope inserted in a stomach for example, to harvest a tissue by introducing a biopsy forceps, for example, into the stomach through a treatment instrument channel provided to the endoscope. Then, a diagnosis is made after the harvested tissue is subjected to a predetermined processing at a pathological department.

However, when harvesting a living tissue, blood flow is instantaneously cut off, resulting in deterioration of the state of the living tissue.

Japanese Patent Application Laid-Open Publication No. 2006-006389 discloses a treatment instrument for endoscope, a living tissue analysis processing system, and a sample harvesting method for tissue analysis processing, which allow the harvested living tissue to be kept in a fresh state and enable an accurate diagnosis to be made.

SUMMARY OF THE INVENTION

A medical apparatus of the present invention comprises: a biopsy treatment instrument insertion path through which biopsy treatment instrument for performing a biopsy on a predetermined region in a body of a subject is inserted, the biopsy treatment instrument insertion path including a projection opening for leading out the biopsy treatment instrument into the body of the subject; a blockage body for blocking the projection opening; and a cooling member for cryogenically cooling a biopsy portion of the biopsy treatment instrument arranged in the vicinity of the blockage body in a state where the biopsy treatment instrument is stored in the biopsy treatment instrument insertion path.

DETAILED DESCRIPTION OF THE PREFERRED EMBODIMENT(S)

Hereinafter, an embodiment of the present invention will be described with reference to the drawings.

Figure 1:
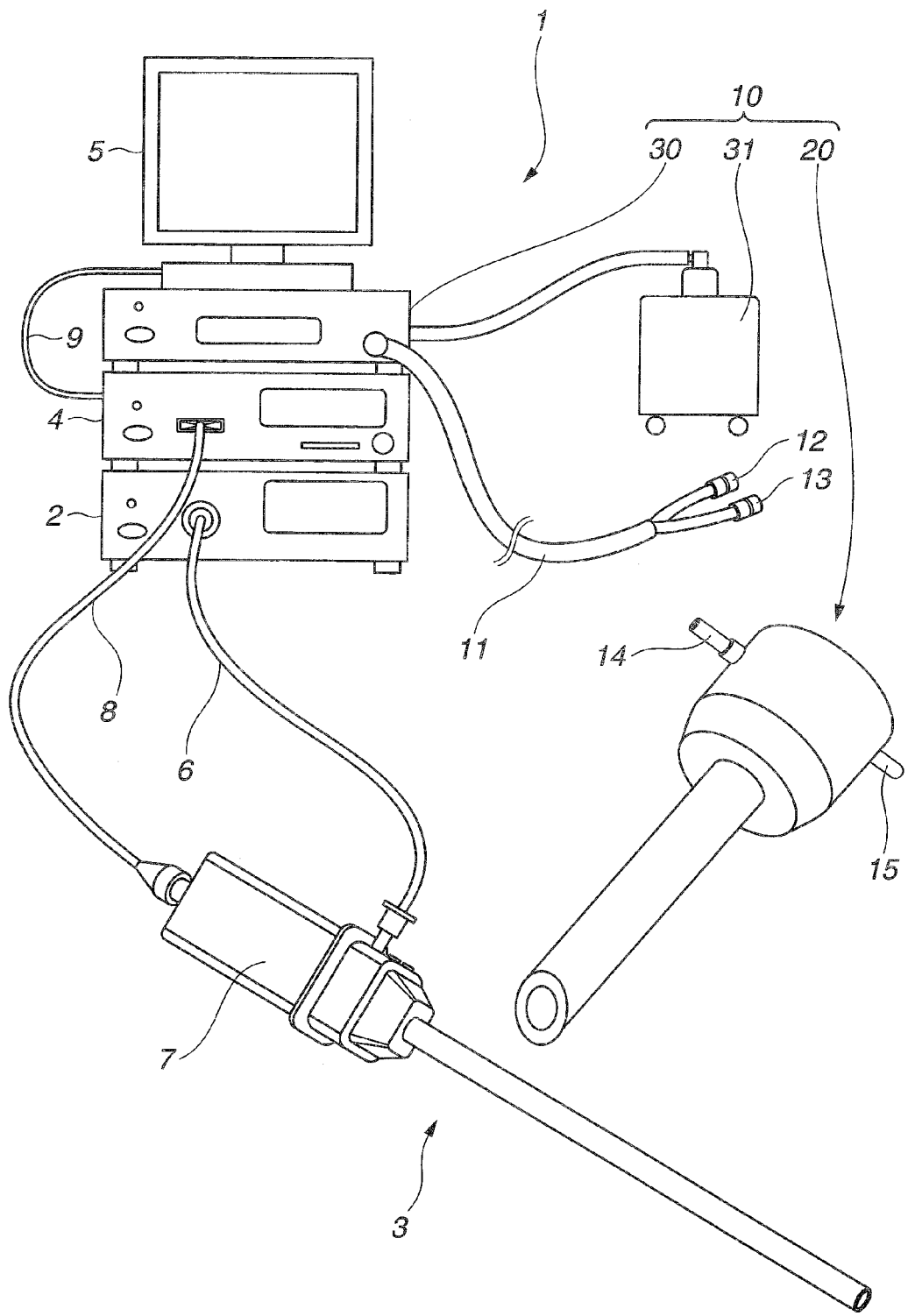
FIG. 1 is a view describing an endoscope system including a first trocar having cooling means.
Figure 2:
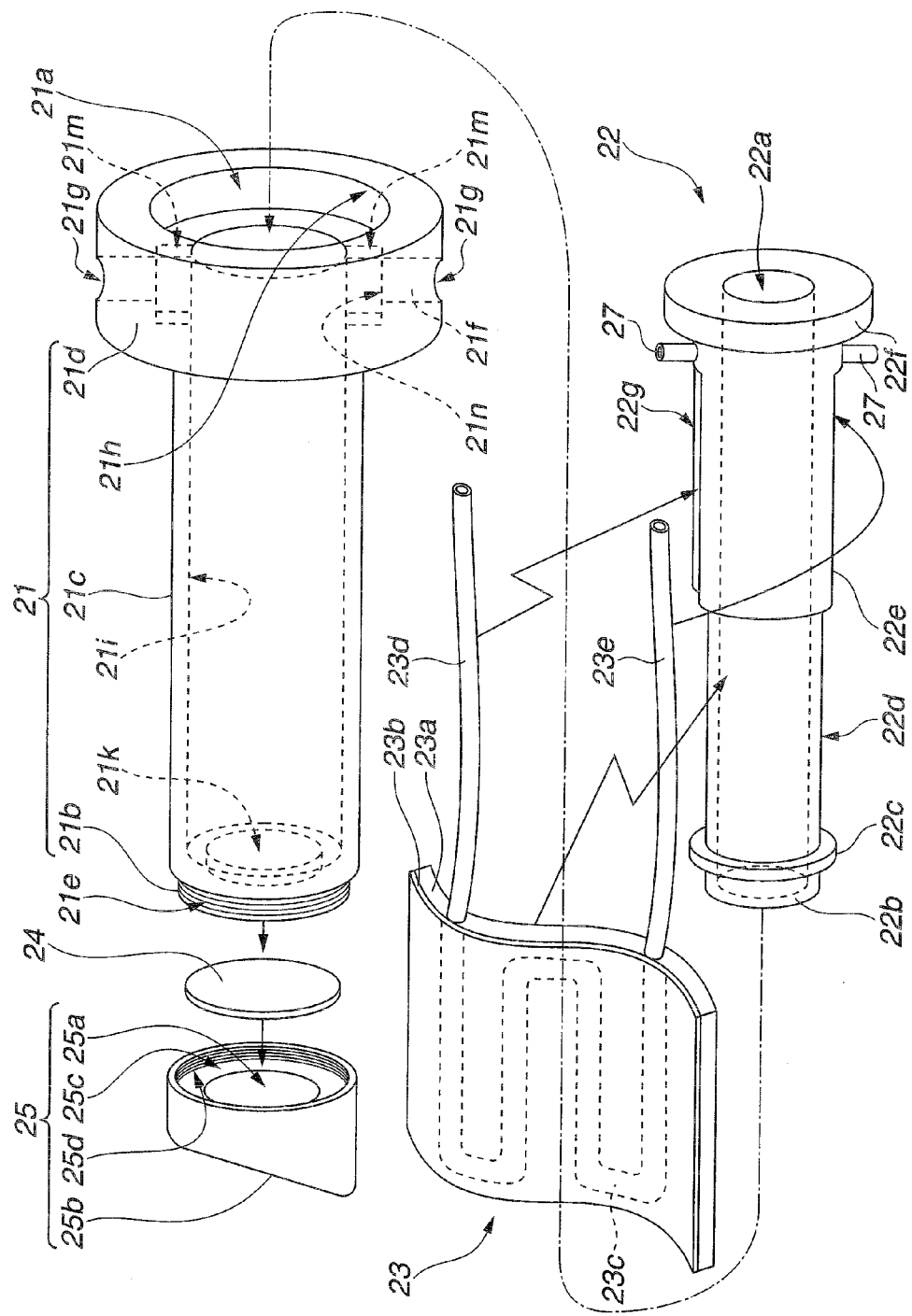
FIG. 2 is an exploded perspective view describing one exemplary configuration of the first trocar.
Figure 3:
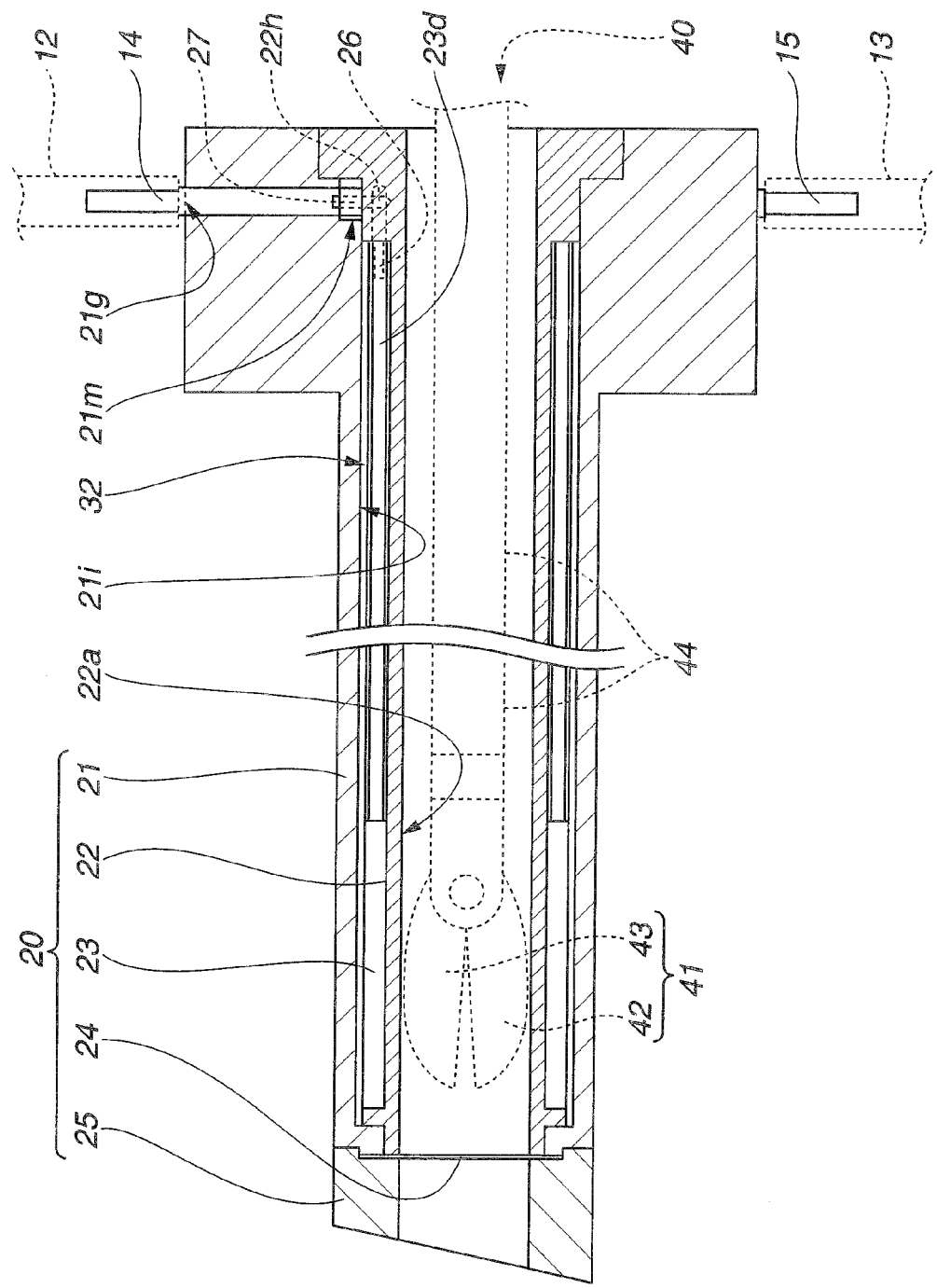
FIG. 3 is a cross-sectional view describing a configuration of the first trocar.
Figure 4:
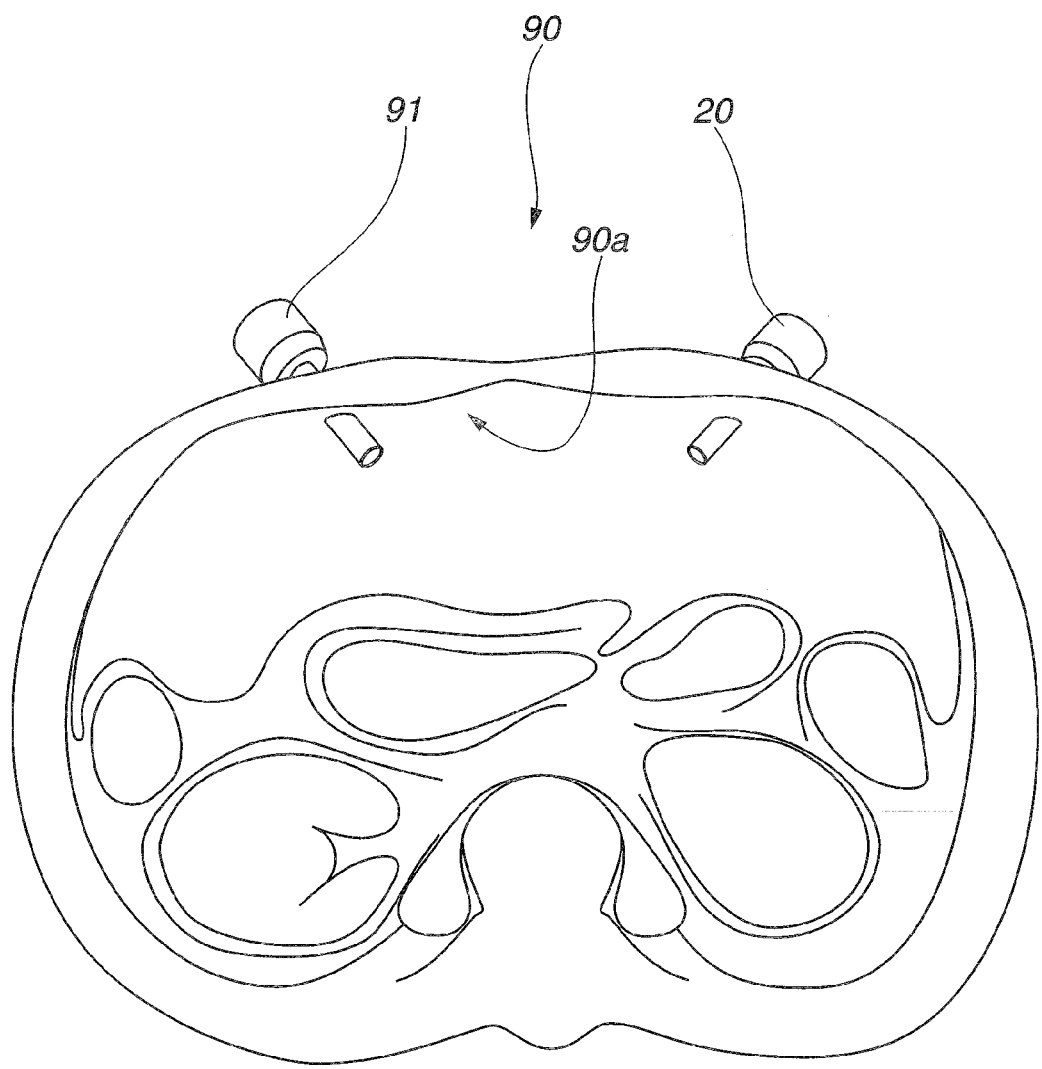
FIG. 4 is a view showing a state where a second trocar and the first trocar are punctured in an abdominal cavity.
Figure 5:
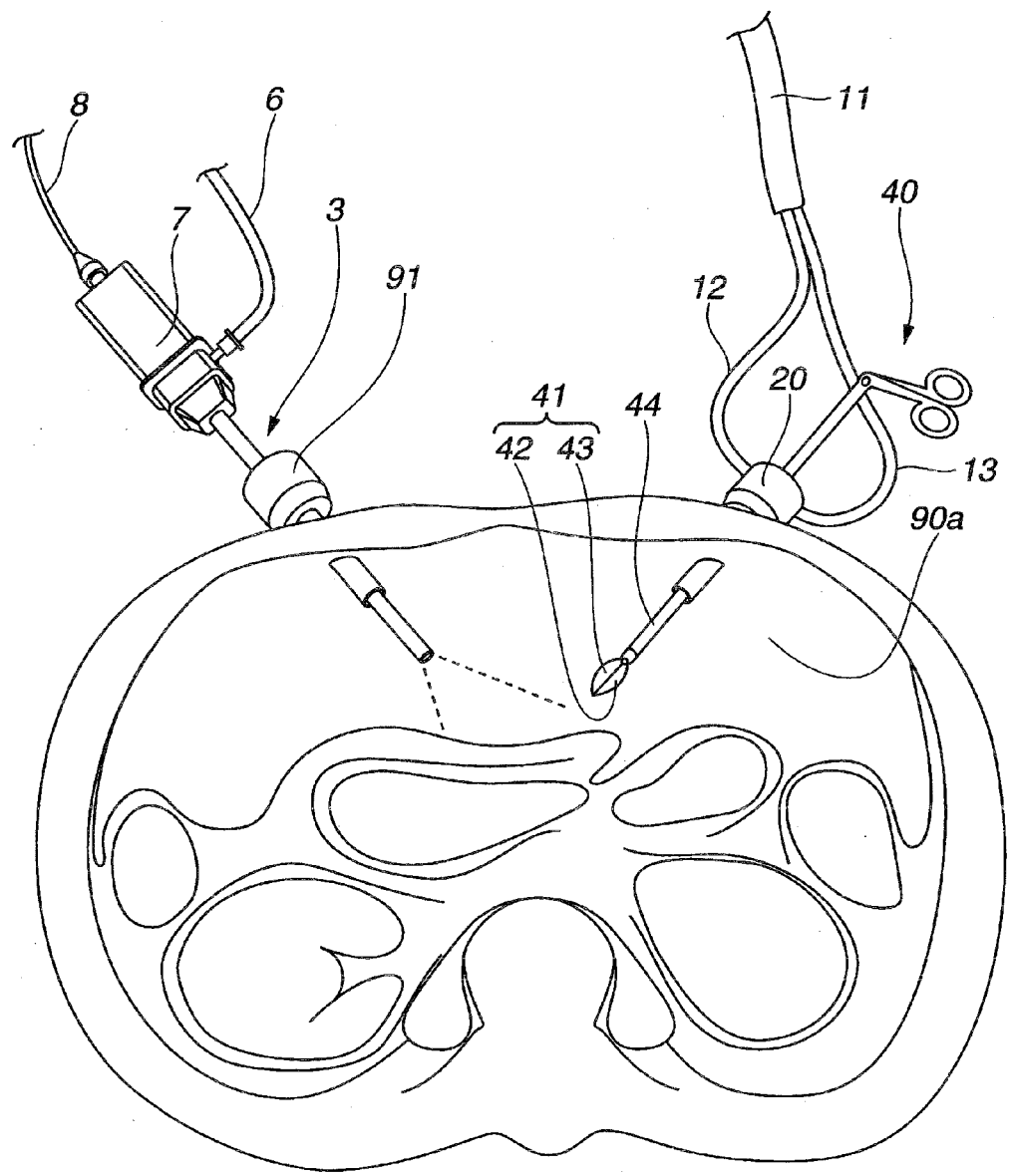
FIG. 5 is a view describing a biopsy with a rigid endoscope introduced in a body cavity through the second trocar and a biopsy forceps introduced in the body cavity through the first trocar.
Figure 6:
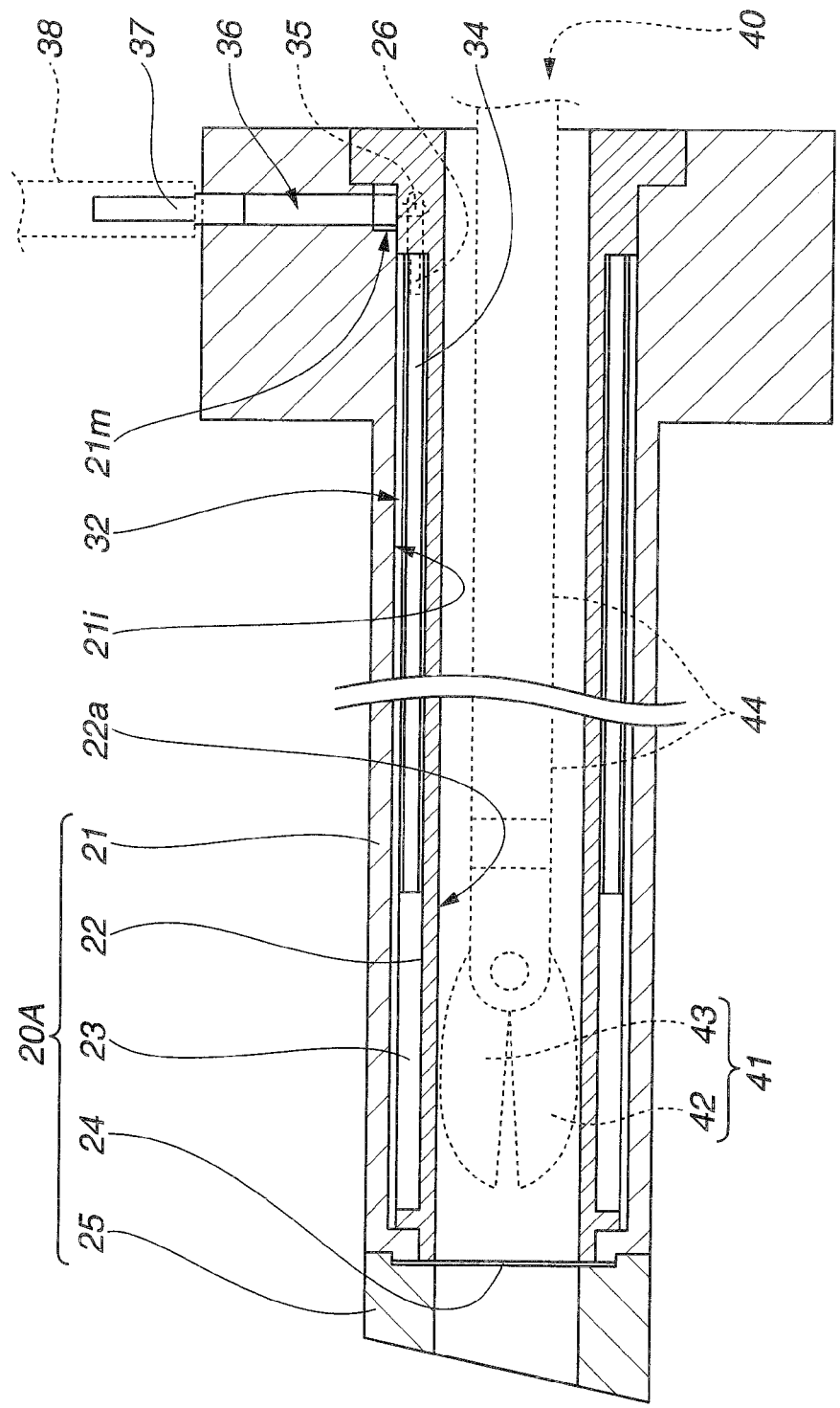
FIG. 6 is a view describing another exemplary configuration of the first trocar.

FIGS. 1 to 6 relate to an embodiment of a medical apparatus: FIG. 1 is a view describing an endoscope system including a first trocar having cooling means; FIG. 2 is an exploded perspective view describing one exemplary configuration of the first trocar; FIG. 3 is a cross-sectional view describing a configuration of the first trocar; FIG. 4 is a view showing a state where a second trocar and the first trocar are punctured in an abdominal cavity; FIG. 5 is a view describing a biopsy with a rigid endoscope introduced in a body cavity through the second trocar and a biopsy forceps introduced in the body cavity through the first trocar; and FIG. 6 is a view describing another exemplary configuration of the first trocar.

FIG. 1 shows an endoscope system 1 for performing a surgery. The endoscope system 1 of the present embodiment is configured by including a light source device 2, a rigid endoscope 3, a camera control unit (hereinafter abbreviated as CCU) 4, a display device 5, and a cooling and harvesting device 10.

The light source device 2 supplies illumination light to an illumination optical system included in the rigid endoscope 3. The light source device 2 and the rigid endoscope 3 are detachably connected to each other by a light source cable 6. The rigid endoscope 3 has, for example, at a proximal end thereof an eyepiece portion to which a camera 7 for the rigid endoscope is connected. Illumination light is supplied from the light source device 2 to the rigid endoscope 3, and an optical image of an observation region illuminated by the illumination light is picked up by the camera 7 for the rigid endoscope connected to the eyepiece portion. The optical image picked up by the camera 7 for the rigid endoscope is photoelectrically converted into an image pickup signal, and the image pickup signal is outputted to the CCU 4 through the image pickup cable 8. The CCU 4 generates a video signal from the transmitted image pickup signal to output the generated video signal to the display device 5. The display device 5 is a liquid crystal display, for example, and receives the video signal outputted from the CCU 4 to display on the screen thereof the endoscopic image of the observation region. The CCU 4 and the display device 5 are detachably connected to each other by a video cable 9.

The cooling and harvesting device 10 is configured by including a first trocar 20 which is a biopsy treatment instrument as medical apparatus including cooling means, a cryogenic fluid supplying device (hereinafter abbreviated as fluid supplying device) 30, and a tank 31. In the present embodiment, the cryogenic fluid is, for example, a low temperature liquid of about −196° C., which is composed of liquid nitrogen and isopentane-propane cryogen for instantly freezing a living tissue.

The fluid supplying device 30 includes a fluid pump and a fluid control portion, both not shown. The fluid supplying device 30 is configured to perform controls to circulate the liquid nitrogen and collect the liquid nitrogen which was being circulated into the tank 31, based on an operation of a foot switch not shown.

The first trocar 20 and the supplying device 30 are connected to each other by a cryogenic fluid supplying tube (hereinafter referred to as fluid tube) 11 for supplying liquid nitrogen. The fluid tube 11 includes an inflow tube 12 and an outflow tube 13. In the present embodiment, the inflow tube 12 is connected to a first connecting member 14 provided to the first trocar 20, and the outflow tube 13 is connected to a second connecting member 15 provided to the first trocar 20.

As shown in FIGS. 2 and 3, the first trocar 20 is configured by including a trocar main body (hereinafter, abbreviated as main body) 21, a cooling cylinder 22, a cooling sheet 23, a lid body 24, and a distal end portion 25.

The distal end portion 25 is a rigid member made of, for example, resin or metal, and includes a through hole 25a through which a treatment instrument such as biopsy forceps passes. The through hole 25a configures a distal-most end portion of a biopsy treatment instrument insertion path. The distal end portion 25 includes an inclined plane portion 25b on a distal end side and a recess portion 25c on a proximal end side. A female screw portion 25d is provided on an inner circumferential surface of the recess portion 25c. Into the female screw portion 25d is screwed a male screw portion 21e of a projection portion 21b, to be described later, provided to the main body portion 21.

The lid body 24 is blockage means configuring a blockage body and is made of paper in the present embodiment. The lid body 24 is placed on a bottom surface of the recess portion 25c configuring the distal end portion 25. The lid body 24 is formed in a circular shape with paper. Specifically, the lid body 24 is formed with paper which can prevent moisture and humidity in a body cavity from entering an insertion hole 22a, to be described later, of the cooling cylinder 22 and which can be penetrated by a biopsy portion 41 of a biopsy forceps 40 stored in the insertion hole 22a moved to a distal end side with a force greater than or equal to a predetermined value by a hand operation of the operator. The biopsy portion 41 includes a pair of rotatable biopsy cups 42, 43.

The cooling sheet 23 is a cooling member as cooling means and is a sheet-shaped cooling member. The cooling sheet 23 is configured by including a sheet main body 23a and a heat-insulating sheet 23b. The sheet main body 23a includes inside thereof a pipe 23c through which the liquid nitrogen circulates. The heat-insulating sheet 23b is provided on one surface side of the sheet main body 23a, and the other surface side thereof is a cooling surface arranged in close contact with a cooling groove 22d in FIG. 2 to be described later.

From one side surface of the cooling sheet 23 are extended two conduits 23d, 23e. One of the conduits 23d is an inflow conduit for making the liquid nitrogen flow into the pipe 23c. The other of the conduits 23e is an outflow conduit for making the liquid nitrogen in the pipe 23c to flow out.

The cooling cylinder 22 is a rigid member made of, for example, resin or metal, and includes the insertion hole 22a, which is a through hole, serving as the biopsy treatment instrument insertion path through which the treatment instrument such as biopsy forceps is inserted. A distal end opening of the insertion hole 22a is a projection opening through which the treatment instrument is led out into the body cavity.

The cooling cylinder 22 is configured by including in the following order from the distal end side, an engaging portion 22b, a first flange portion 22c, the cooling groove 22d, a cylinder main body 22e, and a second flange portion 22f.

The outer diameter dimension of the first flange portion 22c is the same as that of the cylinder main body 22e, and is smaller than the inner diameter dimension of 21i to be described later by a predetermined dimension.

A pair of conduit recess portions 22g is formed on the outer circumferential surface of the cylinder main body 22e. The conduit recess portions 22g are so-called grooves, cross-sections of which have a semicircular shape, a squared C-shape, or a V-shape, in which the conduits 23d, 23e are stored.

The cooling sheet 23 is arranged in the cooling groove 22d. The dimension in the longitudinal axis direction as the width dimension of the cooling groove 22d and the dimension from the outer circumferential surface of the cylinder main body 22e toward the central axis in the longitudinal direction as the depth dimension of the cooling groove 22d are set on the basis of the outer shape of the cooling sheet 23. The depth dimension is set larger than the thickness dimension of the cooling sheet 23 by a predetermined dimension.

A pair of L-shaped flow passages 22h is formed on the cooling cylinder 22, for example. Distal end openings of the L-shaped flow passages 22h are formed inside of the conduit recess portion 22g, and to the distal end openings are fixed conduit bases 26. That is, the conduit bases 26 are provided on end surfaces on the second flange portion 22f side in the conduit recess portions 22g.

On the other hand, proximal end openings of the L-shaped flow passages 22h are formed on the outer circumferential surface on the proximal end side of the cylinder main body 22e, and to the proximal end openings are fixed connecting member bases 27. That is, a pair of connecting member bases 27 is projected from the outer circumferential surface of the second flange portion 22f of the cylinder main body 22e.

The main body portion 21 is a rigid member made of, for example, resin or metal, and includes a cylinder hole 21a as a stepped through hole in which the cooling cylinder 22 is disposed.

The main body portion 21 includes in the following order from the distal end side, the projection portion 21b, a body portion 21c, and a large diameter portion 21d. The male screw portion 21e with which the female screw portion 25d of the distal end portion 25 is engaged is provided on the outer circumferential surface of the projection portion 21b. One-side openings 21g of connecting member holes 21f in which the connecting members 14, 15 are disposed, respectively, are provided on a side surface of the large diameter portion 21d. The connecting member holes 21f correspond to the connecting member bases 27.

The stepped cylinder hole 21a includes in the following order from the proximal end side, a flange recess portion 21h, an elongated hole 21i, and a communicating hole 21k.

The flange recess portion 21h is a flange receiving portion and has an opening on a proximal end surface of the large diameter portion 21d. The second flange portion 22f of the cooling cylinder 22 is arranged in the flange recess portion 21h.

In the elongated hole 21i are loosely arranged the first flange portion 22c and the cylinder main body 22e of the cooling cylinder 22.

The communicating hole 21k communicates the elongated hole 21i with outside. In the communicating hole 21k is arranged the engaging portion 22b of the cooling cylinder 22. The distal end side opening of the communicating hole 21k is a projection opening.

Note that a pair of notched recess portions 21m is formed on the proximal end side of the main body portion 21. The notched recess portions 21m are so formed as to have a predetermined depth from the bottom surface of the flange recess portion 21h. On the notched recess portions 21m are formed the other-side openings 21n of a pair of connecting member holes 21f.

The connecting member bases 27 fixed to the proximal end openings of the L-shaped flow passages 22h are arranged by insertion in the notched recess portions 21m.

Here, assembling of the first trocar 20 will be described.

A worker arranges the cooling sheet 23 in the cooling groove 22d of the cooling cylinder 22 in order to fix the cooling sheet 23 in the cooling groove 22d. At this time, the worker stores the conduits 23d, 23e extending from the sheet main body 23a respectively in the conduit recess portions 22g. At that time, the worker makes the end portions of the conduits 23d, 23e communicate with the conduit bases 26, respectively. Then, the end portions of the conduits 23d, 23e and the base members are watertightly fixed to each other by adhesive bonding, for example.

Moreover, the worker wraps the cooling sheet 23 around the cooling groove 22d such that the cooling surface of the cooling sheet 23 is in close contact with the bottom surface of the cooling groove 22d. Then, the worker integrally fixes the cooling sheet 23 in the cooling groove 22d with a fixing tape not shown. Fixing of the cooling sheet 23 in the cooling groove 22d is thus completed.

Next, the worker mounts to the main body portion 21 the cooling cylinder 22 to which the cooling sheet 23 is fixed. At that time, the worker inserts the engaging portion 22b and the first flange portion 22c of the cooling cylinder 22 to which the cooling sheet 23 is fixed, into the proximal end side of the elongated hole 21i through the flange recess portion 21h configuring the cylinder hole 21a.

Then, the worker inserts the cooling cylinder 22 deeply into the cylinder hole 21a. This allows the cooling sheet 23 fixed in the cooling groove 22d to be introduced in the elongated hole 21i, and thereafter allowing also the cylinder main body 22e to be introduced in the elongated hole 21i.

The worker continues to insert the cooling cylinder 22 deeply into the cylinder hole 21a, thereby allowing the connecting member bases 27 projecting from the outer circumferential surface of the cylinder main body 22e to come close to the flange recess portion 21h.

Here, the worker performs positional adjustment in the rotational direction of the main body portion 21 and the cooling cylinder 22. That is, the worker makes the connecting member bases 27 face the openings of the notched recess portion 21m formed on the bottom surface of the flange recess portion 21h. After the positional adjustment, the worker resumes inserting the cooling cylinder 22 deeply into the cylinder hole 21a.

Then, with the insertion working, the connecting member bases 27 are inserted in the notched recess portions 21m, the engaging portion 22b of the cooling cylinder 22 is inserted in the communicating hole 21k, and the second flange portion 22f is inserted in the flange recess portion 21h.

Then, the distal end surface of the second flange portion 22f contacts the bottom surface of the flange recess portion 21h, thereby allowing the cooling cylinder 22 to be arranged in the cylinder hole 21a of the main body portion 21. At this time, the distal end surface of the engaging portion 22b is arranged closely to but not contacting the lid body 24. In addition, the heat-insulating sheet 23b of the cooling sheet 23 is arranged in the elongated hole 21i so as not to contact the inner circumferential surface of the elongated hole 21i. In addition, the connecting member bases 27 are arranged at predetermined positions of the notched recess portions 21m.

A heat-insulating portions 32 is provided in a gap between the inner circumferential surface of the elongated hole 21i of the main body portion 21 and the outer circumferential surface of the first flange portion 22c of the cooling cylinder 22, in a gap between the inner circumferential surface of the elongated hole 21i of the main body portion 21 and the heat-insulating sheet 23b configuring the cooling sheet 23, and in a gap between the inner circumferential surface of the elongated hole 21i of the main body portion 21 and the outer circumferential surface of the cylinder main body 22e of the cooling cylinder 22.

Note that, in addition to the heat-insulating portion 32, a heat-insulating member may be provided on the outer circumferences of the first flange portion 22c configuring the cooling cylinder 22, of the heat-insulating sheet 23b, and of the cylinder main body 22e.

Next, the worker inserts the connecting members 14, 15 into the connecting member holes 21f from the one-side openings 21g formed on the side surfaces of the large diameter portion 21d. Then, the worker makes the connecting members 14, 15 communicate with the connecting member bases 27, and thereafter watertightly fixes the connecting member 14 and the connecting member base 27 to each other by an adhesive. Similarly, the worker watertightly adheres and fixes the connecting member 15 and the connecting member bases 27 to each other. Thereafter, the worker watertightly fixes the second flange portion 22f and the flange recess portion 21h by adhesive bonding.

Lastly, the worker mounts the distal end portion 25 to the projection portion 21b. At this time, the worker places, as needed, the lid body 24 on the bottom surface of the recess portion 25c configuring the distal end portion 25. Then, in a state where the lid body 24 is placed on the bottom surface of the recess portion 25c, the worker makes the female screw portion 25d of the distal end portion 25 engage with the male screw portion 21e of the projection portion 21b.

This configures the first trocar 20 shown in FIG. 3, wherein the cooling sheet 23 is provided in the main body portion 21 and the distal end portion 25 is mounted to the projection portion 21b. In the first trocar 20, the lid body 24 is held between the bottom surface of the recess portion 25c and the distal end surface of the projection portion 21b.

That is, with the first trocar 20 of the present embodiment, the lid body 24 can be easily changed by detaching the distal end portion 25 from the projection portion 21b of the main body portion 21. In other words, the user can selectively mount the lid body 24 to the first trocar 20.

Description will be made on a procedure to instantly freeze and harvest a living tissue in a body of a subject with the biopsy forceps 40 using the above-described first trocar 20.

When instantly freezing and harvesting the living tissue, the operator punctures the second trocar 91 and the first trocar 20 at predetermined positions in the abdominal region of a patient 90, as shown in FIG. 4. The second trocar 91 has an insertion hole for guiding the rigid endoscope 3 into an abdominal cavity 90a. The first trocar 20 has the insertion hole 22a for guiding the biopsy forceps 40 into the abdominal cavity 90a and the distal end side opening of the insertion hole 22a is blocked by the lid body 24.

Note that the connecting members 14, 15 of the first trocar 20 are connected with the inflow tube 12 and the outflow tube 13, respectively, though the illustrations thereof are omitted. In addition, the second trocar 91 is mounted with one end portion of an insufflation tube not shown. Furthermore, carbon dioxide gas, for example, is injected as insufflation gas in the abdominal cavity 90a for the purpose of ensuring a field of view of the rigid endoscope 3 and an area for operating a surgical instrument and the like.

The operator inserts the rigid endoscope 3 into the second trocar 91 and allows the endoscopic image to be displayed on the screen of the display device 5 to observe a target region. At this time, after specifying a region to be treated such as a lesioned part in the body cavity, the operator starts harvesting the living tissue of the region to be treated.

First, while giving an instruction to bring the main switch of the supplying device 30 into an on-state, the operator arranges an insertion portion 44 of the biopsy forceps 40 in the insertion hole 22a of the first trocar 20.

Next, the operator operates the foot switch to bring the liquid nitrogen into a state to be circulated by the supplying device 30. Then, while the liquid nitrogen in the tank 31 flows in the pipe 23c of the cooling sheet 23 through the inflow tube 12, the connecting member 14, the connecting member base 27, the L-shaped flow passage 22h, the conduit base 26, and the conduit 23d, each of which configuring the inflow passage, the liquid nitrogen circulates through the conduit 23e, the conduit base 26, the L-shaped flow passage 22h, the connecting member base 27, the connecting member 15, and the outflow tube 13, each of which configuring the outflow passage. This allows the cooling groove 22d to be cooled by the cooling sheet 23.

Next, when confirming the circulation of the liquid nitrogen, the operator performs operation to bring the biopsy cups 42, 43 configuring the biopsy forceps 40 into an open state. Then, each of the biopsy cups 42, 43 contacts the inner circumferential surface of the insertion hole 22a in the vicinity of the cooling groove 22d in which the cooling sheet 23 is arranged. This allows the biopsy cups 42, 43 to be cryogenically cooled to equal to or less than −150° C.

Next, when judging that the biopsy cups have been cooled, the operator operates the foot switch to switch the action of the supplying device 30 to a control to collect the liquid nitrogen in the tank 31. Then the operator starts tissue harvesting with the biopsy forceps 40.

That is, the operator performs extrusion operation of the biopsy forceps 40 to guide the biopsy portion 41 into the body cavity. Then, the biopsy portion 41 penetrates the lid body 24 to project into the abdominal cavity 90a, as shown in FIG. 5.

Here, the operator confirms the endoscopic image displayed on the screen of the display device 5 to bring the biopsy portion 41 close to the specified region. Then, the operator performs a predetermined hand operation to harvest the tissue. In harvesting the tissue, since the biopsy cups 42, 43 are cryogenically cooled, the living tissue harvested in the biopsy forceps 42, 43 is instantly (for example, $10^{5\circ}$ C. per second) frozen in a state without anoxia and ischemia. The rapid freezing prevents the cell tissues in the massive tissue harvested by the biopsy cups 42, 43 from being damaged by a formation of a large ice crystal having more than several micrometers in size. That is, an organ in a living body is instantly frozen and harvested alive by biopsy forceps in a desired state.

After that, the operator extracts the biopsy forceps 40 from the first trocar 20 and dips the biopsy portion 41 in the liquid nitrogen to cryopreserve the harvested living tissue. The preserved living tissue is made at −80 to −150° C. as a freeze-substitution fixed sample for optical microscope and electronic microscope which can be observed with an optical microscope and electronic microscope, or as a deep etching replica membrane sample for electronic microscope, at a pathological department.

As a specific example, the living tissue is frozen at −196° C. and preserved, and thereafter freeze-substituted and fixed for twelve to twenty-four hours in two percent, about −80° C. paraformaldehyde-containing acetone solution, or one percent osmium tetroxide-containing acetone solution, and preserved as a living cell tissue morphological image. Note that, as a sample for optical microscope (living cell tissue morphological image), the harvested living tissue is paraffin-embedded and thinly sliced, and thereafter hematoxylin-eosin stained to be examined from diagnostic pathological viewpoint.

Thus, since the cooling sheet including the pipe is provided as the cooling member to the first trocar as the medical apparatus, the liquid nitrogen is circulated in the pipe of the cooling sheet to cryogenically cool the biopsy portion of the biopsy forceps stored in the through hole as the biopsy treatment instrument insertion path of the first trocar, and thereafter the living tissue can be harvested. Thus, by harvesting the living tissue with the cryogenically cooled biopsy portion, the living tissue can be instantly frozen and harvested.

Furthermore, the distal end opening of the through hole serving as the biopsy treatment instrument insertion path of the first trocar is blocked by the lid body, thereby preventing moisture and humidity in the body of the subject from entering the through hole. This prevents that the pair of cooled biopsy cups is frozen by the moisture in the living body and malfunctions thereof.

Furthermore, the gaps as the heat-insulating portions are provided between the inner circumferential surface of the elongated hole and the outer circumferential surface of the first flange portion, between the inner circumferential surface of the elongated hole and the heat-insulating sheet of the cooling sheet, and between the inner circumferential surface of the elongated hole and the outer circumferential surface of the cylinder main body, respectively, thereby preventing the main body portion from being cooled.

In addition, if the lid body is unnecessary, the distal end portion is screwed up to the projection portion of the main body portion without placing the lid body on the bottom surface of the recess portion configuring the distal end portion. Thus, the first trocar having the through hole can be configured.

Note that, when freezing and harvesting a living tissue again, the first trocar is changed to one having the lid body.

Furthermore, the lid body is assumed to be formed with paper in the present embodiment. However, the material of the lid body is not limited to paper, and may be a film member and the like made of synthetic resin, which prevents the moisture and humidity in the body of the subject from entering inside of the through hole.

Moreover, the first trocar is configured to be provided with the cooling sheet as the cooling member in the present embodiment. However, the cooling member is not limited to the cooling sheet for circulating the cryogenic fluid, and may be a heat-exchange device using a peltiert element.

In addition, in the present embodiment, the first trocar 20 has a disassemblable/assemblable structure. However, the trocar 20 may be formed as one structure except the lid body 24 and the distal end portion 25, without assuming diassembling/assembling.

Furthermore, in the present embodiment, the circulation of the liquid nitrogen is controlled by the supplying device 30. However, the circulation of the liquid nitrogen may be a passive circulation by vaporization pressure of a liquid.

FIG. 6 is a view describing the first trocar including a heat-exchange device as the cooling member.

A first trocar 20A shown in FIG. 6 has a heat-exchange device 33 including the peltiert element as the cooling member, instead of the cooling sheet 23. In addition, the endoscope system 1 includes a power supply device not shown instead of the supplying device 30.

The cooling surface of the heat-exchange device 33 is fixed to the cooling groove 22d in a close contact state by adhesive bonding. An electric wire not shown extends from the heat-exchange device 33. The electric wire is inserted through a lead wire conduit 34, an L-shaped path 35, and a connector hole 36 which configure an electric wire insertion hole, and the end portion of the electric wire is connected to a connector portion 37. An electric cable 38 extending from the power supply device is detachably connected to the connector portion 37.

The power supply device incorporates a CPU configuring control means. The CPU is connected to a power supply portion, a switch, and a storage device which are provided in the power supply device, and the peltiert element of the heat-exchange device 33. The switch is operated to turn on and off a driving state of the peltiert element.

Other configurations are the same as those in the above-described embodiment, and the same components are attached with the same reference numerals and the description thereof will be omitted.

Description will be made on a working of the first trocar 20A including the heat-exchange device 33.

In the first trocar 20A, turning on the switch of the power supply device causes the heat-exchange device 33 to be in a driving state. That is, when the power supply device is turned on, electric power is supplied to the peltiert element, thereby driving the peltiert element. Then, the cooling groove 22d is controlled to be cooled to a predetermined temperature.

In this cooling state, the operator performs the operation to bring the biopsy cups 42, 43 of the biopsy portion 41 into an open state as in the above-described embodiment. Then, each of the biopsy cups 42, 43 contacts the inner circumferential surface of the insertion hole 22a in the vicinity of the cooling groove 22d in which the heat-exchange device 33 is arranged, thereby cryogenically cooling the biopsy cups 42, 43.

The same working and effect can be thus obtained by providing the heat-exchange device to the first trocar as the cooling member.

In addition, with the heat-exchange device, a cooling temperature can be appropriately controlled by the CPU provided in the power supply device.

Furthermore, since the heat-exchange device is used as the cooling member, requiring to provide only one electric wire insertion hole through which the electric wire is inserted in the first trocar, the workability in manufacturing the first trocar is simplified, thus providing an inexpensive trocar.

In the above-described embodiment, the medical apparatus including the cooling member is the first trocar. However, the medical apparatus including the cooling member is not limited to the first trocar, but may be, for example, a sheath which is detachably inserted through a trocar and having an insertion hole through which a treatment instrument such as biopsy forceps is inserted, or an endoscope which has a rigid or flexible insertion portion including an treatment instrument channel through which the treatment instrument such as biopsy forceps is inserted.

Figure 7:
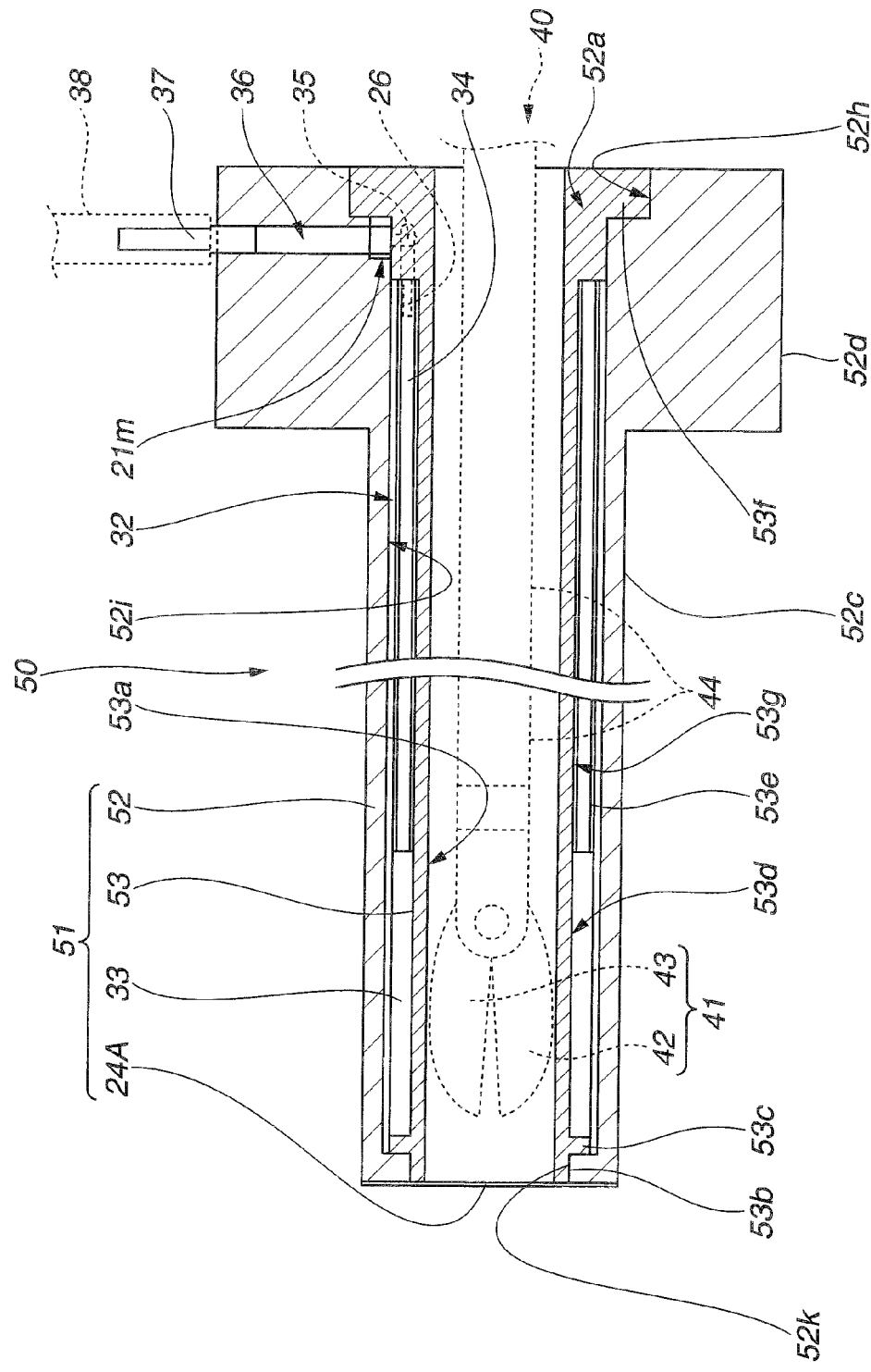
FIG. 7 is a view describing one exemplary configuration of a sheath including cooling means.

FIG. 7 is a view describing one exemplary configuration of the sheath including the cooling means.

A sheath 50 in FIG. 7 includes an insertion portion 51 detachably inserted through the first trocar. The sheath 50 is configured by mainly including an insertion portion main body 52 corresponding to the main body portion 21 of the first trocar 20, a cooling cylinder 53, the heat-exchange device 33, and a lid body 24A.

The lid body 24A is a blockage body. The lid body 24A of the present embodiment is fixed on the distal end surface of the insertion portion 51 by, for example, adhesive bonding by a user.

The cooling cylinder 53 is a rigid member made of, for example, resin or metal, and includes an insertion hole 53a, which is a through hole, serving as the biopsy treatment instrument insertion path through which the treatment instrument such as biopsy forceps is inserted. The distal end opening of the insertion hole 53a is a projection opening through which the treatment instrument is led out in the body cavity.

The cooling cylinder 53 is configured by including in the following order from the distal end side, an engaging portion 53b, a first flange portion 53c, a cooling groove 53d, a cylinder main body 53e, and a second flange portion 53f. A conduit recess portion 53g is formed on the outer circumferential surface of the cylinder main body 22e. The conduit recess portion 53g is the lead wire conduit 34 and is a groove, a cross-section of which has a semicircular shape, a squared C-shape, or a V-shape, in which the electric wire extending from the heat-exchange device 33 is stored.

The heat-exchange device 33 is arranged in the cooling groove 22d. The width and depth dimensions of the cooling groove 53d are set based on the outer shape of the heat-exchange device 33. The L-shaped path 35, for example, is formed in the cooling cylinder 53. A distal end opening of the L-shaped path 35 is formed in the conduit recess portion 53g, and the conduit base 26 is fixed to the distal end opening. On the other hand, a proximal end opening of the L-shaped path 35 is formed on the outer circumferential surface of the proximal end side of the cylinder main body 53e, and the proximal end opening communicates with the connector hole 36 to be described later of the insertion portion main body 52.

The insertion portion main body 52 is a rigid member made of, for example, resin or metal, and has a cylinder hole 52a as a stepped through hole in which the cooling cylinder 53 is disposed.

The insertion portion main body 52 includes in the following order from the distal end side, a main body portion 52c and a large diameter portion 52d that configure the insertion portion 51. On the side surface of the large diameter portion 52d is formed the connector hole 36 in which a connector portion 37 is disposed. The connector hole 36 communicates with the proximal end opening of the L-shaped path 35, as described above.

The stepped cylinder hole 52a includes a flange recess portion 52h, an elongated hole 52i, and an engaging hole 52k. The flange recess portion 52h is a flange receiving portion, in which the second flange portion 53f of the cooling cylinder 53 is arranged. In the elongated hole 21i are arranged the first flange portion 53c and the cylinder main body 53e of the cooling cylinder 53. In the engaging hole 52k is arranged the engaging portion 53b.

Then, the cooling cylinder 53 including the heat-exchange device 33 is arranged in the cylinder hole 52a of the insertion portion main body 52, and thereafter integrally fixed to the cylinder hole 52a by adhesive bonding, for example. Thus the sheath 50 including the insertion portion 51 is configured.

The lid body 24A is adhered and fixed as needed by a user on the distal end surface of the insertion portion 51 configuring the sheath 50. By adhering and fixing the lid body 24A, the distal end opening of the insertion hole 53a is blocked, which prevents the moisture and humidity in the body of the subject from entering inside of the through hole 53a.

The heat-exchange device is thus provided to the sheath, which enables freezing and harvesting of a living tissue to be easily performed by exchanging the sheath inserted in the first trocar. Other working and effect are the same as those of the above-described first trocar.

Figure 8:
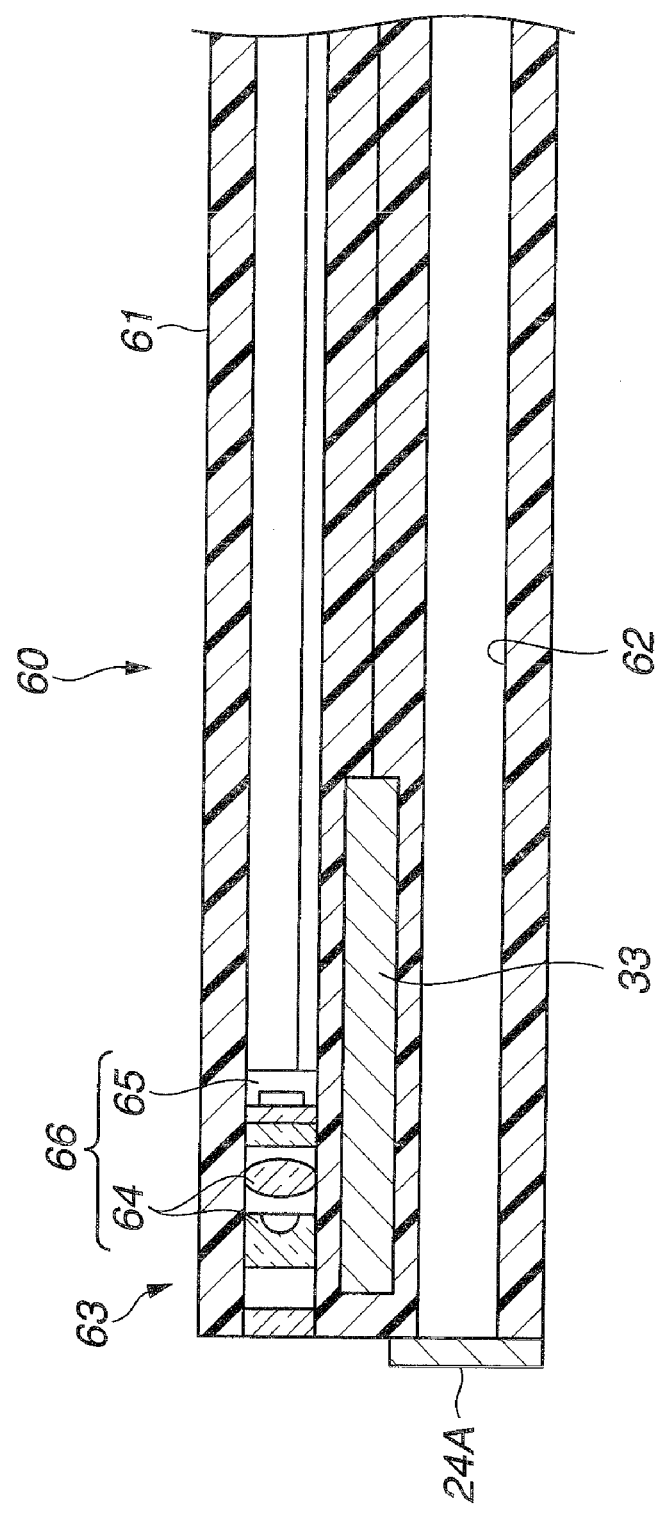
FIG. 8 is a view describing one exemplary configuration of an endoscope including cooling means.

FIG. 8 is a view describing one exemplary configuration of an endoscope including the cooling means.

An endoscope 60 in FIG. 8 has in an insertion portion 61 thereof a treatment instrument insertion channel 62, not shown, through which the biopsy forceps is inserted, for example.

At a distal end portion 63 of the insertion portion 61 are provided an observation optical system 66 configured by including a plurality of optical lenses 64 and an image pickup device 65, an illumination optical system configured by including optical elements such as LEDs not shown, and the heat-exchange device 33 as the cooling member. A distal end opening of the treatment instrument insertion channel 62 is blocked by the lid body 24A as the blockage body.

The distal end opening of the treatment instrument insertion channel 62 is blocked as needed by a user. That is, the user adheres and fixes the lid body 24A at a predetermined position on the distal end surface of the insertion portion to block the distal end opening of the treatment insertion channel 62, thereby preventing the moisture and humidity in the body of the subject from entering inside of the treatment instrument insertion channel 62.

Thus, by providing the heat-exchange device at the distal end portion of the insertion portion of the endoscope, a living tissue can be frozen and harvested during endoscopic observation.

Note that, though not shown, the living tissue freezing and harvesting apparatus may be configured by providing a capsule endoscope with a storing portion for storing a treatment instrument with which a biopsy is performed on a predetermined region of a body of a subject, a heat-exchange device for cooling the biopsy portion of the treatment instrument stored in the storing portion, and a lid body for blocking inside of the storing portion and outside of the capsule. In this capsule endoscope, the heat-exchange device also serves as a cryopreservation device for cryopreserving the frozen and harvested living tissue.

Note that the present invention is not limited to the above-described embodiment, and various modifications are possible without departing from the scope of the invention.

In the above-described embodiment, the living tissue is cryogenically and instantaneously frozen and harvested. However, the cryogenically and instantaneously frozen and harvested tissue is not limited to a human tissue, and may be animal tissue.

What is claimed is:

1. A medical apparatus comprising:
    a biopsy treatment instrument to be introduced into a body of a subject, for performing a biopsy on a predetermined region; and
    a medical trocar including:
        a biopsy treatment instrument insertion path through which the biopsy treatment instrument is inserted,
        a projection opening for leading out the biopsy treatment instrument into the body of the subject in a predetermined region,
        a blockage body for blocking the projection opening, and
        a cooling member, arranged in the vicinity of the blockage body, for cryogenically cooling a biopsy portion of the biopsy treatment instrument stored in the biopsy treatment instrument insertion path.

2. The medical apparatus according to claim 1, wherein the medical trocar instrument includes a heat-insulating portion.

3. The medical apparatus according to claim 1, wherein the cooling member includes a cryogenic fluid supplying device for circulating cryogenic fluid.

4. The medical apparatus according to claim 1, wherein the cooling member is a peltier element.

5. A medical apparatus comprising:
    a biopsy treatment instrument to be introduced into a body of a subject for performing a biopsy on a predetermined region by a pair of biopsy cups operable to be opened and closed; and
    a medical trocar including:
        a trocar main body having a cylindrical shape with openings at distal and proximal ends to include an elongated hole formed therein,
        a rigid distal end portion, provided at the distal end of the trocar main body, including a through hole through which the biopsy treatment instrument passes,
        a lid body, provided at the distal end portion for blocking the through hole, and penetrated by the biopsy cups by moving the biopsy treatment instrument,
        a cooling cylinder, inserted into the elongated hole of the trocar main body, including an insertion hole communicating with the through hole of the distal end portion, and
        a cooling member in the form of a sheet arranged in a cooling groove formed between the trocar main body and the cooling cylinder inserted into the trocar main body.

6. The medical apparatus according to claim 5, wherein the biopsy cups contact an inner circumferential surface of the cooling cylinder where the cooling groove is formed.

\* \* \* \* \*